(12) United States Patent
Abela

(10) Patent No.: US 7,731,731 B2
(45) Date of Patent: Jun. 8, 2010

(54) CATHETER FOR CLEARING PASSAGES IN A PATIENT

(76) Inventor: George S. Abela, 6201 Windrush La., E. Lansing, MI (US) 48823

( * ) Notice: Subject to any disclaimer, the term of this patent is extended or adjusted under 35 U.S.C. 154(b) by 727 days.

(21) Appl. No.: 11/154,812

(22) Filed: Jun. 17, 2005

(65) Prior Publication Data
US 2006/0287667 A1 Dec. 21, 2006

(51) Int. Cl.
*A61M 29/00* (2006.01)
(52) U.S. Cl. ...................................... 606/200
(58) Field of Classification Search ................. 606/159, 606/200, 114, 127, 128, 191, 1
See application file for complete search history.

(56) References Cited

U.S. PATENT DOCUMENTS

| | | | |
|---|---|---|---|
| 4,445,509 A | 5/1984 | Auth et al. | |
| 4,646,736 A | 3/1987 | Auth et al. | |
| 4,850,957 A | 7/1989 | Summers | |
| 4,867,156 A | 9/1989 | Stack et al. | |
| 4,990,134 A | 2/1991 | Auth | |
| 5,059,211 A | 10/1991 | Stack et al. | |
| 5,306,286 A | 4/1994 | Stack et al. | |
| 5,314,407 A | 5/1994 | Auth et al. | |
| 5,364,393 A | 11/1994 | Auth et al. | |
| 5,370,653 A | 12/1994 | Cragg | |
| 5,895,400 A | 4/1999 | Abela | |
| 5,902,263 A | 5/1999 | Patterson et al. | |
| 6,383,206 B1 * | 5/2002 | Gillick et al. | ............ 606/200 |
| 6,676,683 B1 * | 1/2004 | Addis | ............ 606/200 |

OTHER PUBLICATIONS

ISSN 0735-1097/02, vol. 39, No. 5, dated Mar. 6, 2002; "Multicenter Evaluation of Carotid Artery Stenting With a Filter Protection System", Mubarak et al.
2002 American Heart Association, Inc. "Percutaneous Left Atrial Appendage Transcatheter Occlusion to Prevent Stroke in High-Risk Patients with Atrial Fibrillation", Sievert et al.

* cited by examiner

*Primary Examiner*—Todd E Manahan
*Assistant Examiner*—Eric Blatt
(74) *Attorney, Agent, or Firm*—Miles & Stockbridge P.C.; David R. Schaffer, Esq.

(57) ABSTRACT

In accordance with an embodiment of the present invention, a system for widening passages in the body of a patient includes a member extendable into a patient with a proximal end and a distal end with a tip and a hollow interior extending therebetween; bristles adjacent the distal end of the member such that rotation of the proximal end of the member causes rotation of the bristles to remove material from walls of pre-existing passages in the patient and, all of the bristles are inclined away from the tip of the distal end as they extend out from the distal end; a guide wire having a proximal end and a distal end disposed within the hollow interior and extendable into the patient; and a non-rotating capture member coaxially aligned with and fixed near the guide wire distal end to be disposed within the hollow interior and extendable into the patient.

38 Claims, 5 Drawing Sheets

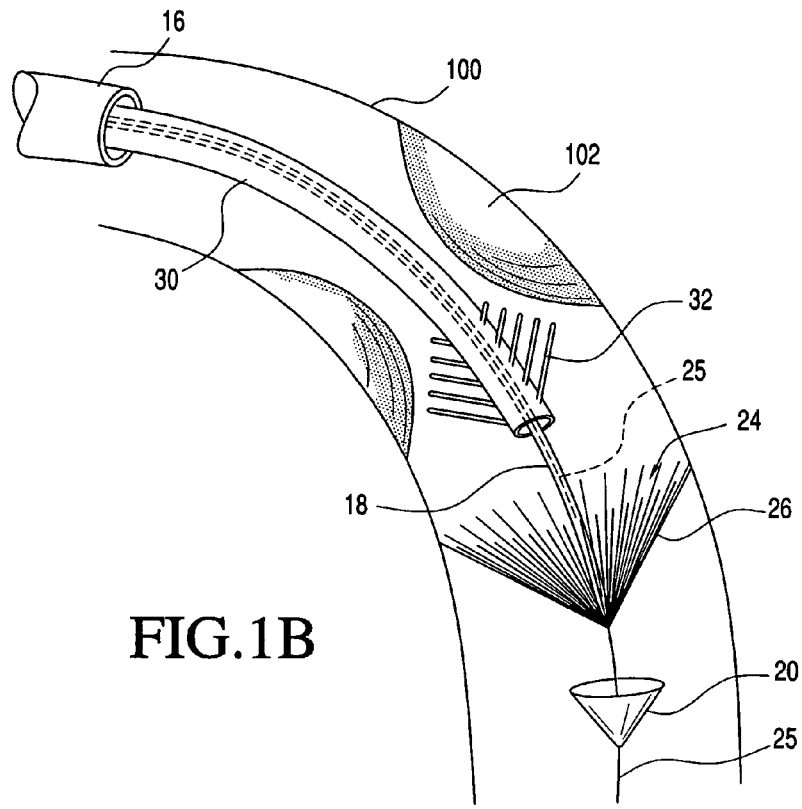
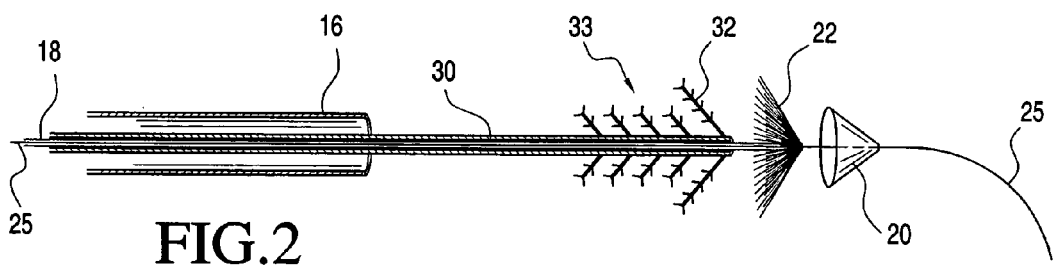
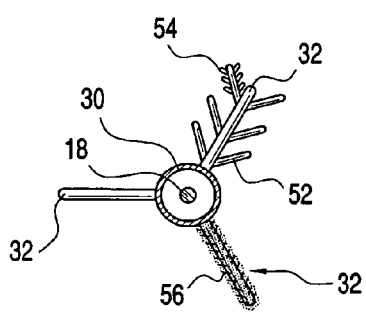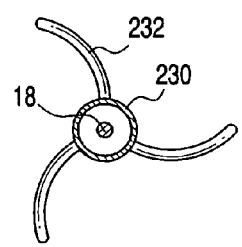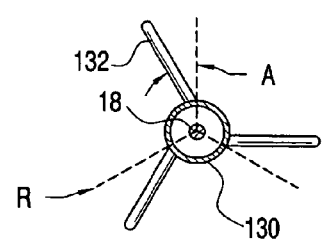
FIG.1B
FIG.2
FIG.3    FIG.4    FIG.5

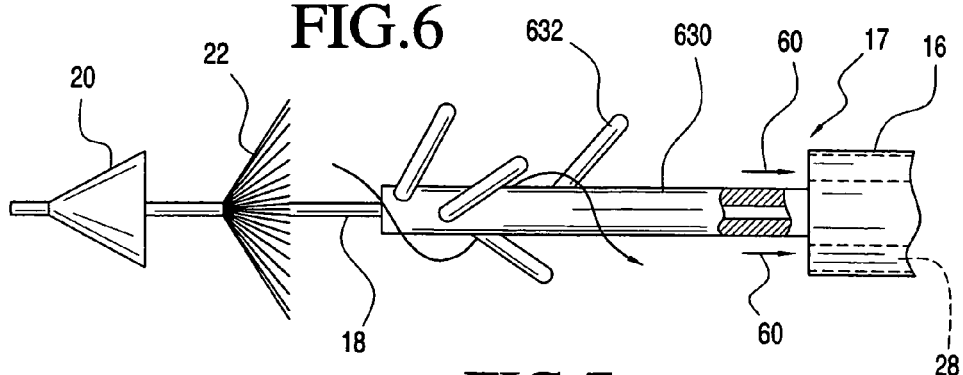
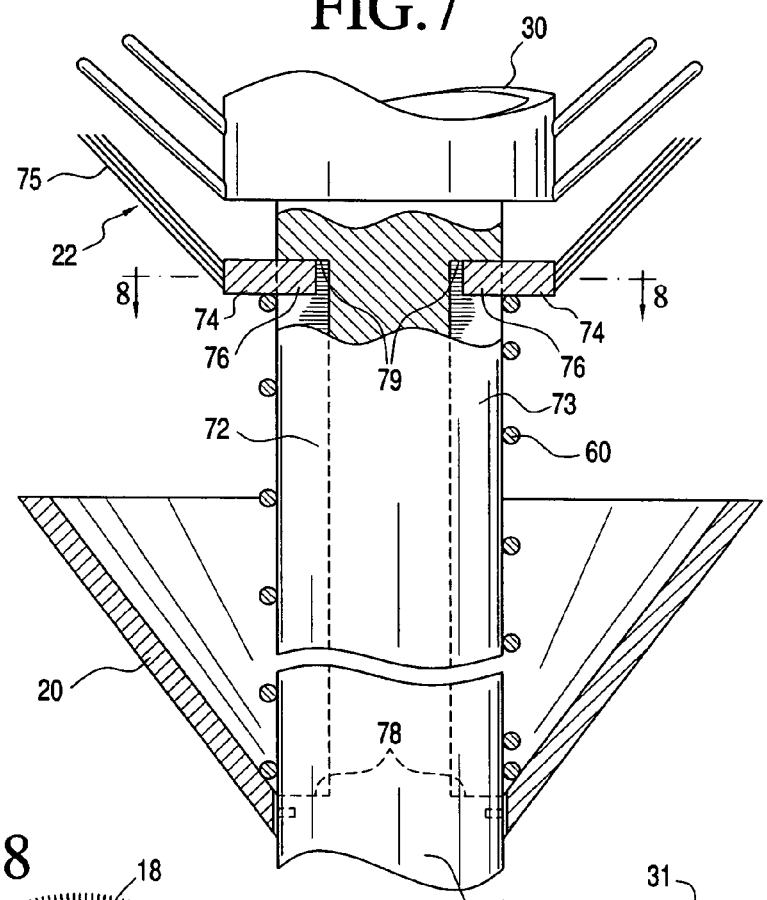
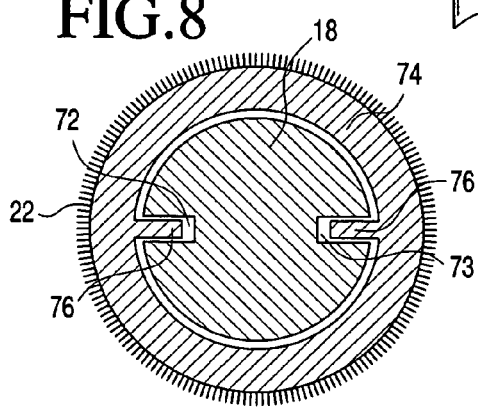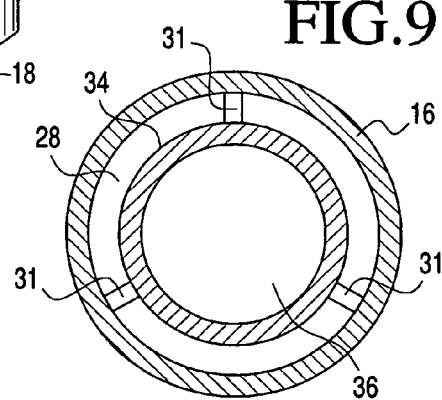

CATHETER FOR CLEARING PASSAGES IN A PATIENT

FIELD OF THE INVENTION

The present invention relates to a system and method for widening or clearing passages in a patient, and more specifically to a catheter system with bristles and a method of use of same to widen and/or clear passages.

BACKGROUND OF THE INVENTION

Within the human body are various passages, which convey fluids. Material may build up on the walls of such passages such that partial blockages may occur. Indeed, such partial blockages, if left untreated, may eventually become complete blockages. Whether the blockages are partial or complete, there usually are adverse health consequences associated therewith.

In the cardiovascular system, in particular, a vein or artery may be partially or completely blocked. The veins or venous blood vessels may be blocked (hereinafter meaning partially or completely blocked) by a blood clot called a thrombus. The arteries or arterial blood vessels may also be blocked by a thrombus. In either a vein or artery, plaque or other such blockages should be treated using one or more medical procedures.

The following patents are noted:

| Inventor | Patent No. | Issue Date |
| --- | --- | --- |
| Auth | 4,445,509 | May 1, 1984 |
| Auth | 4,646,736 | Mar. 3, 1987 |
| Summers | 4,850,957 | Jul. 25, 1989 |
| Stack et al | 4,867,156 | Sep. 19, 1989 |
| Auth | 4,990,134 | Feb. 5, 1991 |
| Stack et al | 5,059,211 | Oct. 22, 1991 |
| Stack et al | 5,306,286 | Apr. 26, 1994 |
| Auth et al | 5,314,407 | May 24, 1994 |
| Auth et al | 5,364,393 | Nov. 15, 1994 |
| Cragg | 5,370,653 | Dec. 6, 1994 |
| Abela | 5,895,400 | Apr. 20, 1999 |

The Stack patents disclose catheters for removing plaque from the wall of an artery using blade elements and devices to work with such cutting catheters.

The Auth patents show various structures for removing calcified material. The use of diamond dust covered abrasive devices, a cutting tool with spirally shaped cutting flutes, and electrical ablation are among the techniques disclosed.

The Cragg patent and the Summers patent both show cutting catheter systems and methods. Cragg has rotatable soft flexible bristles, whereas Summers has a cutting arrangement with a continuous filament brush and an alternate cutting blade design.

The Abela patent discloses a catheter with a rotatable bristle arrangement carried on a sweep catheter extending along a guide wire.

Cutting devices often must be sized to fit the particular passage which is being treated. In other words, one must use a different size cutter for every different size of vessel. Disadvantageously, one must then have more than one cutter available and must determine the correct size before putting the cutter into the patient, such that the correct size cutter is used. Use of a cutter that is too small will not remove all of the plaque or other built-up material. Use of a cutter that is too large increases the chances of damaging healthy tissue on the wall of the passage.

Some prior devices for cutting or removing material from the walls of passages in a patient are constructed such that they may damage healthy tissue on the wall of the passage even if they are the right size. Depending on the characteristics of the blocking material, the adjacent healthy tissue, and the cutting device (for example, if the cutting device is too rigid), damage may occur when cutting.

A further problem with some prior arrangements is that materials removed from the wall of a blood vessel, for example, can create problems downstream from the original blockage. Removed materials can resettle downstream and create a partial or complete blockage at a new location. Depending on the size of the material pieces, a heart attack, stroke, or other health problems can result from attempting to remove blood vessel obstructing material.

Chemical solutions have been proposed for use in dissolving the pieces. Depending upon the chemical used, this may require that the passage be blocked by a balloon for a considerable period of time. A catheter-controlled balloon may be used downstream from where the material is being removed. The balloon prevents removed material from passing by it until the material is dissolved. Suction devices have also been used for removing material.

The Abela patent discloses a catheter system that overcomes several of the disadvantages found in prior devices. A sweep catheter having a set of bristles on its distal end is proposed for use in removing all or portions of a thrombus located in a vein or artery. This system is effective at removing the material while eliminating or reducing the risk of damage to blood vessel tissue.

Accordingly, a catheter system and method that addresses one or more of the above-noted deficiencies or disadvantages would be desirable.

SUMMARY OF THE INVENTION

In accordance with an embodiment of the present invention, a system for widening passages in the body of a patient may include a member extendable into a pre-existing passage of the patient. The member may have a proximal end, a distal end and a hollow interior extending therebetween. The system may also include movable bristles disposed on the member adjacent the distal end of the member such that rotation of the proximal end of the member causes rotation which, in turn, rotates the bristles. The bristles are operable upon rotation to remove material from walls of the pre-existing passages within which the bristles rotate and, can be axially moved along the passage to clean the artery or vein. The bristles are inclined and extend away from the distal end of the member. The system may further include a guide wire having a proximal end and a distal end that may be moveably disposed within the hollow interior of the member and extendable into the patient. A non-rotating capture member is coaxially aligned with, fixed to and near the distal end of the guide wire. The guide and capture member are adapted to be disposed within the member and are extendable into the patient beyond the distal end of the member by the guide wire.

BRIEF DESCRIPTION OF THE DRAWINGS

The above and other features of the present invention will be more readily understood when the ensuing detailed description of the preferred embodiments is considered in conjunction with the accompanying drawings, wherein like characters represent like parts throughout the several views.

FIG. 1B is a simplified side view of a catheter system with some portions removed and others shown in cross-section, in accordance with another embodiment of the present invention.

FIG. 2 is a simplified side view of a distal portion of the catheter system, in accordance with an embodiment of the present invention.

FIG. 3 is a simplified end view of the distal end of a sweep catheter, in accordance with an embodiment of the present invention.

FIG. 4 is a simplified end view of the distal end of a sweep catheter, in accordance with another embodiment of the present invention.

FIG. 5 is a simplified end view of the distal end of a sweep catheter, in accordance with yet another embodiment of the present invention.

FIG. 6 is a simplified side view with portions removed of the distal end of the catheter system showing a bristle pattern on the distal end of a sweep catheter, in accordance with an embodiment of the present invention.

FIG. 7 is a substantially schematic side view of the distal ends of a sweep catheter and a guide wire in a catheter system, in accordance with an embodiment of the present invention.

FIG. 8 is a cross-sectional view taken along line 8-8 of FIG. 7.

FIG. 9 is a cross-sectional view taken along line 9-9 of FIG. 1.

DETAILED DESCRIPTION OF THE PREFERRED EMBODIMENTS

Figure 1A:
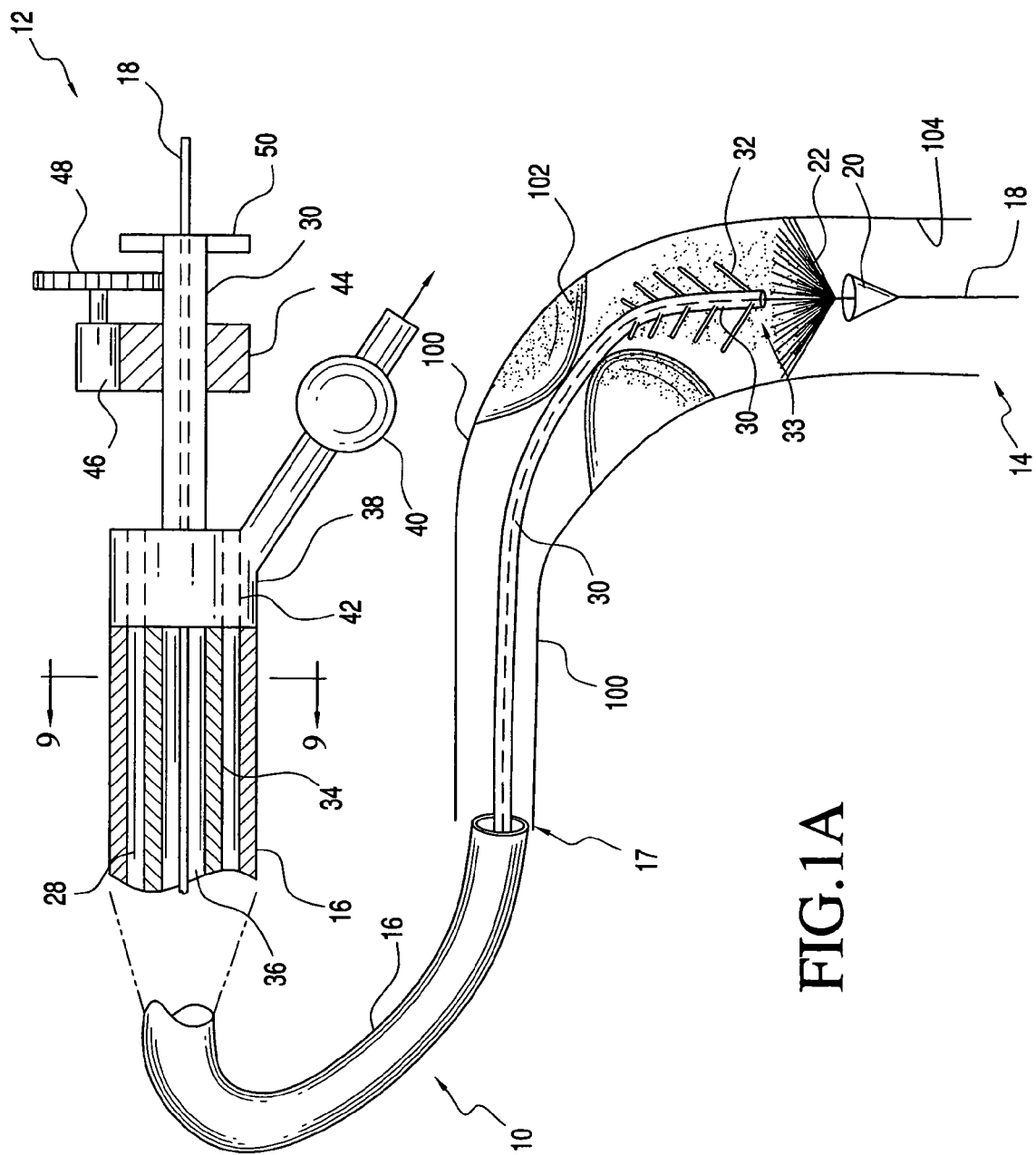
FIG. 1A is a simplified side view of a catheter system with some portions removed and others shown in cross-section, in accordance with an embodiment of the present invention.

In accordance with some embodiments of the present invention, a catheter system and method for removal of material from the walls of passages in the body of a patient may be provided. Specifically, the system and method may provide for removal of material from the walls of blood vessels. For example, the component may be used advantageously to remove a fresh thrombus (i.e., generally, a gelatinous, softer thrombus), an organized thrombus (i.e., an older thrombus having a more rubbery nature) and/or soft plaque material (i.e., a much older thrombus, deposit and/or softer lipid material deposit). In addition, the component may also remove often seen blockages in bypass grafts, i.e., soft pasty material.

In accordance with some embodiments of the present invention, a catheter system and method may provide for the removal of material from the walls of passages without requiring a close match between the size of a removing component (i.e., a component that removes material from the wall by cutting, abrading or otherwise) and the size of a passage. This is due to the conforming nature of the arterial channel.

In accordance with some embodiments of the present invention, a catheter system and method may provide for removal of material from the walls of passages with little or no risk, or reduced risk, of damage to body tissues.

In accordance with some embodiments of the present invention, a catheter system and method may provide for removal of material from the walls of passages with little or no risk, or reduced risk, of damage to body tissues.

In accordance with some embodiments of the present invention, a catheter system and method may provide for removal of material from the walls of passages quickly.

The above and other features of the present invention may be realized by a catheter system for widening passages in a patient's body. A guide is extendable into a patient to define a proximal (rearward) end and a distal (forward) end.

In accordance with an embodiment of the present invention, the catheter system may employ a guide catheter, through which a guide wire may extend, with the guide wire extending past an open distal end of the guide catheter when positioned in the blood vessel at a desired location. A hollow sweep catheter having bristles attached thereto at a distal end thereof may surround the guide wire and be sized so as to be capable of protruding past the distal end of the guide catheter. Also extending within the interior of the sweep catheter may be a fixed brush catheter having a set of bristles at a distal end thereof, and being arranged to be positioned downstream of the bristles of the sweep catheter.

In accordance with an embodiment of the present invention, a shroud or wrap may be provided to be positioned downstream of the brushes of both the fixed brush catheter and the sweep catheter. The shroud or wrap may be employed to be drawn over the brushes once the clearing or widening operation is completed, and prior to the brushes being retracted into the guide catheter. A small cap may be employed distal of or in place of the shroud or wrap, which, when retracted toward the brushes, will cause the brushes to deform or bend back toward a proximal end of the catheter, and to closely surround the sweep catheter.

In accordance with an embodiment of the present invention, the sweep catheter may be operated in much the same manner as is disclosed in the previously cited Abela patent, which is hereby expressly incorporated by reference herein, although constructional differences are present. Notably, the tips of the bristles may be rounded, to avoid or to minimize sticking to the arterial wall. The fixed brush catheter may be designed, by selection of the number, size, density, and geometry of the bristles thereon, to effectively act as a filter to trap particles removed from the blood vessel tissue by the sweep catheter. The fixed brush catheter, at the same time, may allow blood flow to continue through the blood vessel being treated.

In accordance with an embodiment of the present invention, the shroud or wrap, which may be initially placed in position downstream of the fixed brush catheter and the sweep catheter, is capable of being retracted (moved in a direction toward a proximal end of the catheter) to enshroud the bristles and to thus trap any particles held by the bristles, so that the fixed brush catheter and sweep catheter can be retracted into guide catheter without releasing the particles into the downstream flow of blood.

In accordance with an embodiment of the present invention, the shroud or wrap may be made of proximal and distal rings comprising wires made of memory metal, and having a mesh sock extending between the rings. The use of memory metal for the rings will allow the shroud to enter the body in a low temperature (e.g., room temperature) contracted state, and, upon entering the bloodstream outside the distal end of the guide catheter, the rings will be heated by the blood and change shape into an expanded ring shape. In addition, one or more stiffening members may run between the proximal and distal rings to bias the two rings away from each other.

In accordance with a potentially less complex embodiment of the present invention, a small metal cap of substantially conical shape would be employed in place of the shroud. Upon completion of the cleaning procedure, the cap would be drawn over the radial inward portions of the fixed bristles, causing these to collapse or deform inwardly. The fixed bristles will, in turn, force the bristles on the sweep catheter inwardly as well. The fixed brush catheter and sweep catheter would then be retracted into the guide catheter for withdrawal from the patient.

FIG. 1A is a simplified side view of a catheter system with some portions removed and others shown in cross-section, in accordance with an embodiment of the present invention. In FIG. 1A, a catheter system 10 is shown to have a proximal end 12 and a distal end 14, which is shown, somewhat schematically, positioned within a blood vessel 100, such as an artery, of a patient. Thus, catheter system 10 is shown in position to perform an operation to remove or reduce the size of a thrombus 102 that is partially obstructing artery 100.

It should be noted that the principal focus of the discussion herein will relate to the removal or reduction in size of a thrombus and other debris (soft plaque, organized thrombus, etc.) within a blood vessel and/or vein graft. However, the catheter system and method of the present invention may also be used for clearing, partially clearing or widening (hereinafter, collectively, "clearing") other passages in the body of a patient having a wide variety of diameters, especially where material (for example, plaque, etc.) has built up or accumulated on the walls of a passage. Such other passages include other passages in the vascular system. Further, the terms "obstruction" and "blockage" as used herein are intended to include complete obstructions or blockages, as well as partial obstructions or blockages.

In FIG. 1A, proximal end 12 of catheter system 10 is disposed outside of the body of the patient, whereas distal end 14 is generally positioned in the vicinity of thrombus 102 or other obstruction found in artery 100. Catheter system 10 may include a guide catheter 16 having a passage defined therethrough to allow various devices to be inserted into artery 100. In FIG. 1A, guide catheter 16 is shown positioned such that its distal end 17 is located upstream of thrombus 102. It is to be recognized, however, that guide catheter 16 may also be inserted past one or more obstructions or blockages (e.g., other thrombus'), provided sufficient clearance exists, so as to be positioned within a suitable distance of the thrombus of interest, for example, thrombus 102.

In FIG. 1A, a guide wire and 18 is substantially coaxially aligned with extends from proximal end 12 of catheter system 10 and protrudes through distal end 17 of guide catheter 16, with a tip of the guide wire extending past thrombus 102. In accordance with an embodiment of the present invention, in using catheter system 10, guide wire 18 may first be inserted into the patient and advanced to the position shown in FIG. 1A, specifically, past or downstream of the partial blockage or thrombus 102. Once guide wire 18 is positioned past thrombus 102, guide catheter 16 may then be advanced along and around guide wire 18 until its distal end 17 is positioned upstream of thrombus 102, as illustrated in FIG. 1A. Guide wire 18 may include a conical cap 20 coaxially aligned with and attached near a distal end of guide wire 18. Conical cap 20 may be comprised of a non-biologically reactive metal, alloy and/or other material, may be in a solid and/or a porous configuration, and may be sized to be passed through and out of and retracted back into the passage of guide catheter 16. Guide wire 18 may also include a fixed brush implemented as a set of fixed bristles 22 circumferentially attached to and coaxially aligned with guide wire 18 proximal of conical cap 20. In general, fixed bristles 22 are substantially stiff, extend and/or fan out to and are in contact around an inner wall 104 of artery 100, and are angled back toward proximal end 12 of catheter system 10. As such, in their extended position fixed bristles 22 may approximate a substantially conical shape. Fixed bristles 22 are of sufficient density to provide a mechanism to capture debris flowing toward a proximal side of bristles 22 while permitting blood and other fluids in artery 100 to pass through. For example, the density of fixed bristles 22 may determine which size particles may be trapped therein, for example, >30 to 100 micron particles. In addition, tips of fixed bristles 22 may be rounded, e.g., by melting the tips, to lessen the likelihood that the tips may stick into and/or damage interior wall 104 of artery 100. Fixed bristles 22 may further be detachably attached to guide wire 18 to permit cap 20 to move proximally toward and contact a distal side of fixed bristles 22 to cause fixed bristles 22 to angle (i.e., fold) farther back toward the proximal and of guide wire 18 to permit being retracted back into guide catheter 16.

In FIG. 1A, a sweep catheter 30 has an open-ended, hollow interior that extends essentially coaxially with guide wire 18 inside of guide catheter 16, and may have a plurality of bristles 32 disposed at a distal end 33 thereof. The configuration and orientation of these bristles may be substantially the same as is disclosed in U.S. Pat. No. 5,895,400, which has been expressly incorporated by reference herein. Essentially, the longest bristles are preferably adjacent distal end 33 of sweep catheter 30, and progressively shorter bristles are provided proximally from distal end 33. Bristles 32 are preferably angled back toward proximal end 12 of catheter system 10.

In FIG. 1A, and also considering FIG. 9, proximal end 12 of catheter system 10 includes a suction channel 28 with ribs 32 connecting it to a tubular wall 34, which has a central channel 36 therein. Central channel 36 accommodates guide wire 18 and sweep catheter 30 within it, but those components are not shown within the cross sectioned part of guide catheter 16 for ease of illustration. An adaptor 38 allows a suction pump 40 to apply a suction to the annular channel 28. Adaptor 38 is an end cap with an annular space 42 therein to communicate between the upstream side of pump 40 and the annular channel 28. Additionally, adaptor 38 has a central opening therein to allow sweep catheter 30 to extend therethrough.

In FIG. 1A, sweep catheter 30 is rotatably mounted in journal 44 with motor 46 operable to rotate sweep catheter 30 by way of gear or friction wheel 48 coupling to the outer surface of sweep catheter 30. A handle 50 is mounted to the proximal end of sweep catheter 30 for free rotation therebetween. Thus, when a doctor moves sweep catheter 30 in or out using ring like handle 50, the handle itself will not be rotating from motor 46. Sweep catheter 30, in FIG. 1A, may more broadly be considered as a flexible member that may be inserted into a patient and having bristles 32 on its distal end 33.

The tips of fixed bristles 22 may be rounded (FIGS. 3-6), such that gouging and/or sticking of the tips to the arterial wall is minimized or avoided. The tips may be melted and quickly cooled to form the rounded shape. In FIG. 1A, in accordance with an embodiment of the present invention, sweep catheter 30 is rotatably mounted in journal 44 with motor 46 being operable to rotate sweep catheter 30 by way of gear or friction wheel 48 being operatively coupled to an outer surface of the sweep catheter 30. In addition, a handle 50 is mounted to the proximal end of the sweep catheter, with the handle being freely rotatable relative to sweep catheter 30. This will allow the physician to advance or retract the sweep catheter using handle 50, and this action will not interfere with any rotation of the catheter being effected by the motor 46 and gear/friction wheel 48.

In accordance with another embodiment of the present invention, in FIG. 1B a fixed brush catheter 24 may include guide wire 18, which may be hollow and have a passage defined therethrough and through which a separate central wire 25 may extend. Guide wire 18 may extend within sweep catheter 30 and may have an array 26 of fixed bristles secured at its distal end or tip. The array of fixed bristles 26 may be positioned by guide wire 18 downstream of sweep bristles 32 and upstream of conical cap 20 on separate central wire 25 inside the artery 100, as shown in FIG. 1B In FIG. 1B, the bristles of array 26 on fixed brush catheter 24 are selected and positioned or arranged so that the array 26 can operate as a downstream filter to trap particles that have been removed from thrombus 102 by bristles 32 on sweep catheter 30, while allowing blood to flow through and past the array 26 of bristles. Generally, the bristles are formed in a substantially single annular ring, with bristles extending radially outwardly from guide wire 18 and angled back toward the proximal end of catheter system 10, thereby collectively forming a relatively shallowly configured conical surface. The length of the bristles is preferably selected to be long enough so that the array spans substantially the entire cross-sectional area of an artery 100 or other passage in which the catheter system is inserted.

The number, size, and/or density of, and/or the radial distribution of, the bristles may be selected so as to effectively trap particles of a certain size. For example, it might be desired to trap only those particles that are greater than 30 microns in size. In such a case, the density and distribution of the bristles may be selected such that spacings (viewed in cross-section) of no greater than 30 microns exist between any adjacent bristles. In a case where, for example, only particles greater than 100 microns in size are to be trapped, a less dense array, having spacings of up to 100 microns between bristles, may be employed. Regardless of the specific particle size to be trapped, the density and distribution of the bristles will be determined by what acceptable particle size can be accommodated by a patient's distal circulation system without causing a blockage.

FIG. 2 is a substantially schematic side view of a distal portion of the catheter system, in accordance with an embodiment of the present invention. In FIG. 2, bristles 32 are distributed over a lengthwise extending portion of distal end 33 of sweep catheter 30. Bristles 32 extend out variable distances from distal end 33 of sweep catheter 30. Specifically, for example, bristles 32 may extend further from distal end 33 of sweep catheter 30 the closer they are to the tip (i.e., the distal most point on the guide catheter). As shown in FIGS. 1A, 1B and 2, bristles 32 extend out variable distances from distal end 33 of sweep catheter 30 because the bristles adjacent the tip are longer than ones further from the tip. However, all bristles 32 might, alternatively, have the same length, but have different angles relative to the catheter central axis such that they extend out variable distances from the distal end of the sweep catheter. Regardless of their length and/or orientation, as described herein, bristles 32 may be made of various plastics, including for example, a soft nylon and polyethylene, and/or metal including stainless steel, copper, and NITINOL.

In FIGS. 2 and 3, as well as in all other figures described herein, bristles 32 may be sputter-coated to increase the cutting effect of the bristles. For example, bristles 32 may be sputter-coated using techniques known in the art with a variety of materials, including for example, carbon, diamond and/or gold. Bristles sputter-coated with carbon become very smooth and stronger than the un-coated bristles. Bristles sputter-coated with gold become stronger and slightly abrasive. Bristles sputter-coated with diamond become fairly stiff and very abrasive. As a result, in some embodiments of the present invention, bristles 32 may be used to remove blockages caused by soft thrombus' as well as calcified material.

In FIG. 2, cap 20, fixed bristles 22 and bristles 32 are shown fully extended in position to be used to remove material from an inside wall of a passage in a patient. Specifically, cap 20 is located distal of fixed bristles 22 on guide wire 18 and both of which are located distal of bristles 32 on sweep catheter 30.

FIG. 3 is a simplified cross-sectional end view of the distal end of a sweep catheter, in accordance with an embodiment of the present invention. With reference to FIGS. 2 and 3, bristles 32 may include sub-bristles 52 extending out from them and even sub-sub-bristles 54 extending out from sub-bristles 52. For ease of illustration only a few sub-bristles 52 and a few sub-sub-bristles 54 are shown. However, all bristles 32 may be constructed identically as well as in mixed configurations, e.g., but not limited to, alternating rows and/or columns of bristles 32 only and bristles 32 with one or more levels of sub-bristles 52. Also, for ease of illustration, a sputter coating 56, for example, a rough sputter coating such as diamond, is shown on one bristle of bristles 32. Of course, sputter coating 56 may cover all of bristles 32 as well as all sub-level bristles and associated outer portion of sweep catheter 30 beneath and adjacent to bristles 32. Additionally, although only three sizes of bristle construction are shown (i.e., bristles 32, sub-bristles 52, and sub-sub-bristles 54), more different sizes could be used by having the sub-sub-bristles having sub-sub-sub-bristles thereon, etc.

As can be seen in FIGS. 4, 5, and 6 the shape and orientation of bristles 32 of sweep catheter 30 may take on various shapes and orientations. FIG. 4 shows an alternate sweep catheter 130 with bristles 132 extending out from the distal end at an angle A relative to the radial lines R. In contrast, FIG. 3 arrangement has the bristles extending along radial lines (not shown). Except as discussed, the FIG. 4 sweep catheter 130 would be constructed and operable like sweep catheter 30 of FIG. 3.

The bristles illustrated in FIG. 5 are curved such that, together with the angled back orientation of the bristles, the bristles tend to move pieces/particles of thrombus material separated from the blood vessel toward the distal end of guide catheter 16, where the material can be suctioned out of the blood vessel, as will be discussed later in this specification. In FIG. 5, in accordance with an alternate embodiment of the present invention, a sweep catheter 230 has curved bristles 232 which, like bristles 132 of catheter 130 in FIG. 4, operate like a corkscrew so that removed thrombus materials are propelled toward distal end 17 of guide catheter 16 from rotation of bristles 232. Guide catheter 16 may then be used to suction materials out of the patient.

FIG. 6 is a partial cross-sectional, side-view of a sweep catheter, in accordance with another embodiment of the present invention. Specifically, in FIG. 6, a sweep catheter 630 may have bristles 632 arranged in a spiral or helix pattern. In such a configuration, the rotation of bristles 632 will tend to pull the material separated from an artery wall in the illustrated spiral or helical path, toward distal end 17 of guide catheter 16. Any of the types of bristles disclosed herein may be arranged on the sweep catheter in this spiral or helical pattern. With reference to FIG. 6, sweep catheter 630 may have bristles 632 arranged in a spiral pattern (i.e., different flights of bristles, like the pattern for a spiral staircase) such that rotation of bristles 632 tends to pull material in the illustrated spiral path towards guide catheter 16. The spiral bristle pattern may use the type of bristles illustrated in any of FIGS. 3-5. The materials may be pulled into an annular suction channel 28 in sweep catheter 630 as illustrated by the arrows 60.

FIG. 7 is a partial cut-away and cross-sectional side view of a guide wire, fixed bristle and cap assembly configuration, in accordance with an embodiment of the present invention. In FIG. 7, a portion of the distal end of guide wire 18 is shown to include two substantially longitudinally opposing channels 72, 73 in which fixed bristles 22 may surround and be moveably connected to guide wire 18 in channels 72, 73. Fixed bristles 22 may include a ring 74 that surrounds guide wire 18 and a plurality of bristles 75 attached around an outer circumference of ring 74 and angling toward the proximal end of guide wire 18. Ring 74 may include tabs 76, 77 that slidingly engage channels 72, 73 to permit distal and proximal movement of fixed bristles 22 while preventing rotation about guide wire 18. Although guide wire 18 and ring 74 are shown to have two channels and two tabs, respectively, other embodiments are contemplated in which only one as well as three or more channels and tabs, respectively, may be used.

In FIG. 7, a distal end of cap 20 is shown to be attached to guide wire 18 just distal of distal ends 78 of each of channels 76, 77 and biased apart from fixed bristles 22 by a biasing member 60, for example, a spring, which are shown with ring 74 adjacent proximal ends 79 of channels 76, 77. Although shown biased apart in FIG. 7, embodiments are contemplated in which fixed bristles 22 and cup 20 are not biased apart. Ring 74 is also shown adjacent distal end 33 of sweep catheter 30 and bristles 32. In operation, cap 20 may be pulled proximally by guide wire 18 and channels 72, 73 may move unimpeded proximally past fixed bristles 22 until the proximal open end of cap 20 contacts a distal side of the plurality of bristles 75 at which time the plurality of bristles 75 may be urged proximally and fold toward guide wire 18. Cap 20 may continue moving proximally until distal sides of tabs 76, 77 abut distal ends of channels 72, 73 and/or an interior surface of cap 20. In this position, fixed bristles 22 should be in a substantially folded back position to permit the unified proximal movement of fixed bristles 22 and cap 20 toward distal end 33 of sweep catheter 30 and bristles 32. As fixed bristles 32 contact a distal side of bristles 32, bristles 32 begin to fold back in the proximal direction toward the outer surface of sweep catheter 30. When fixed bristles 22 contact distal end 33 of sweep catheter 30, bristles 32 will be in a substantially completely folded back position to permit the withdrawal of sweep catheter and guide wire 18 into guide catheter 16 for removal from the patient without damaging the interior walls of the passage.

FIG. 8 is a cross-sectional view of FIG. 7 along lines 8-8, in accordance with an embodiment of the present invention. In FIG. 8, guide wire 18 is shown with two substantially oppositely opposed channels 72, 73. However, as noted above, embodiments with different numbers of channels are contemplated, including one, two, three or more. Likewise, alternative channel designs are contemplated, for example, U-shaped, V-shaped, rounded, T-shaped, etc. to permit complementary tab 76, 77 shapes to be inserted therein. In FIG. 8, channels 72, 73 are shown as substantially square grooves in which complementary substantially square tabs 76, 77 from ring 74 may be inserted and travel in the proximal and distal directions relative to guide wire 18.

FIG. 9 is a cross-sectional view taken along lines 9-9 of FIG. 1 showing the proximal end of catheter system 10. In FIG. 9, suction channel 28 has ribs 31 connecting it to tubular wall 34 having central channel 36 therein. Central channel 36 accommodates guide wire 18 and sweep catheter 30 within it, but those components are not shown within the cross sectioned part of guide catheter 16 for ease of illustration.

Figure 10C:
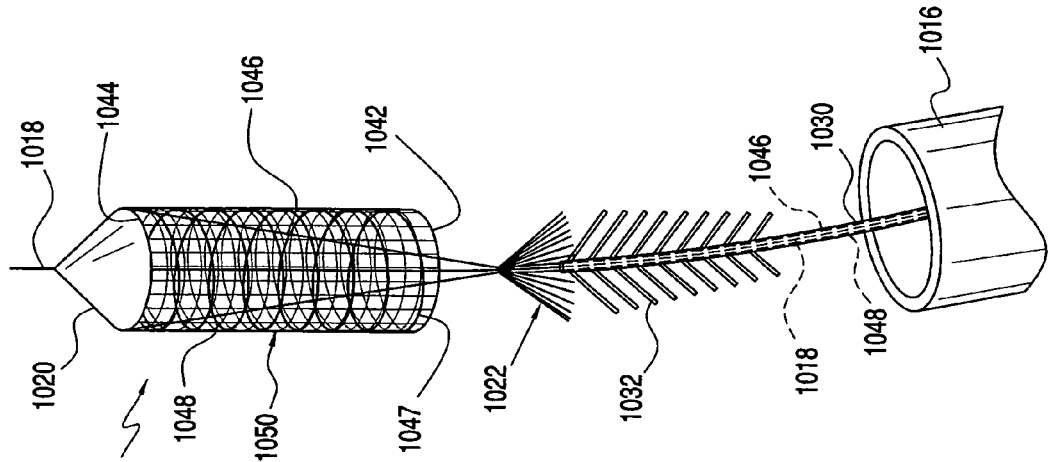
FIGS. 10 A-C are simplified side views of the distal portion of the catheter system, in accordance with an embodiment of the present invention.
Figure 10B:
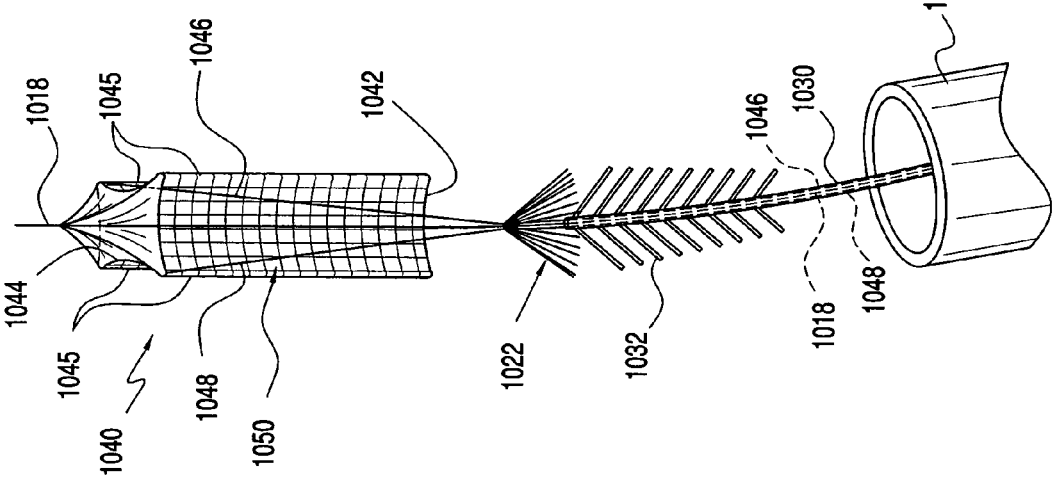
Figure 10A:
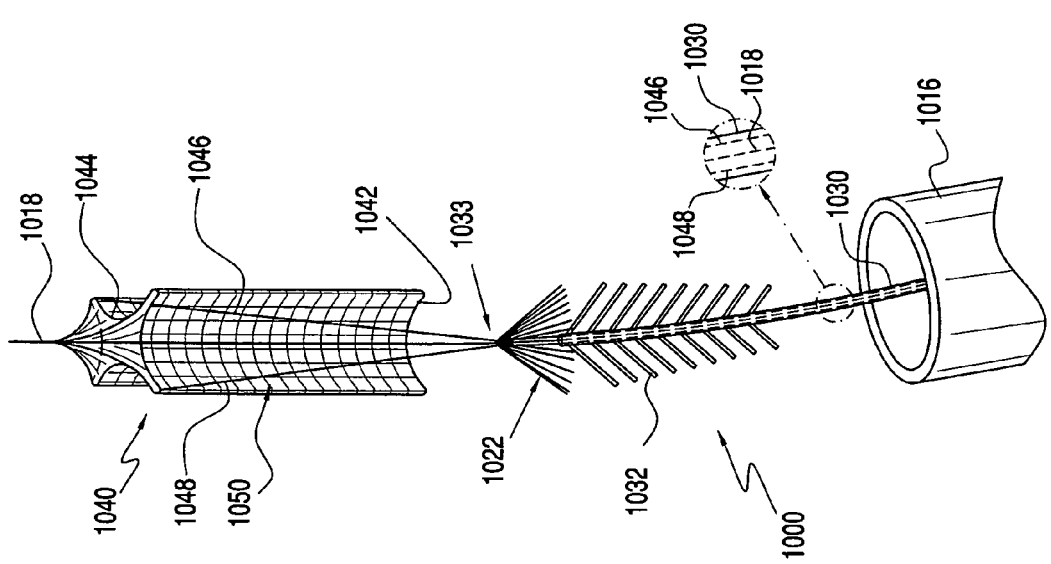

FIGS. 10A, 10B, and 10C are simplified side views of the distal portion of a catheter system, in accordance with another embodiment of the present invention. For clarity and ease of explanation, the following description will be primarily in relation to FIG. 10A. However, the explanation is equally applicable to FIGS. 10B and 10C, except where noted to the contrary. In FIG. 10A, a distal portion 1000 of a catheter system is illustrated and includes a guide catheter 1016, a guide wire 1018, a fixed bristle element 1022, a sweep catheter 1030, and a shroud and/or wrap 1040. Guide catheter 1016 includes a distal end that defines an opening into a lumen that runs from the distal end to and is open at a proximal end (not shown) of guide catheter 1016. Sweep catheter 1030 is disposed in the lumen of guide catheter 1016 and includes a hollow interior running between and open at a distal end 1033 and a proximal end (not shown). Sweep catheter 1030 also includes a plurality of bristles 1032 disposed on an exterior distal surface of sweep catheter 1030. Plurality of bristles 1032 have the same and/or similar characteristics as bristles 32 described above in relation to FIGS. 1 to 6.

In FIG. 10A, guide wire 1018 is disposed in the hollow interior of sweep catheter 1030 and includes a proximal end and a distal end. Fixed bristle element 1022 is attached to guide wire 1018 near its distal end and comprises a plurality of bristles that are angled toward the proximal end of guide wire 1018 and of sufficient length and density to close off and filter out particles of material in a passage, for example, an artery in a patient, into which fixed bristle element 1022 is deployed while permitting fluids in the passage in which the particles are floating to pass through.

In FIG. 10A, shroud 1040 may be positioned downstream, i.e., distally, of fixed bristle element 1022 and may be coaxially aligned with and surrounding guide wire 1018. Shroud 1040 may be open at both ends and/or open at a proximal end and closed at a distal end of shroud 1040. Although a cap 1020 is not shown in FIG. 10A or 10B for ease of illustration, it is shown in FIG. 10C at the distal end of shroud 1040. Alternatively, although not shown in FIGS. 10A-C, the distal end of shroud 1040 also may be attached by separate wires to guide wire 1018. In general, the separate wires would be attached to guide wire 1018 distal to fixed bristles 1022 and be of sufficient length to permit shroud 1040 to be deployed distally of fixed bristles 1022 during use and still be able to be pulled proximally to cover fixed bristles 1022 and bristles 1032. Shroud 1040 may be constructed of first and second wire rings 1042, 1044, also termed proximal and distal rings, respectively, and a mesh shroud material 1050 extending peripherally around first and second wire rings 1042, 1044, and extending axially along the distance separating first and second wire rings 1042, 1043.

In FIG. 10A, first and second wire rings 1042, 1044, and cap 1020, if included, may be made of a memory metal that responds to changes in temperature, also referred to herein as a thermally-reactive or a thermally-activated memory metal. In addition, one or more stiffening members which also may be made of a thermally-activated memory metal, may run between first and second wire rings 1042, 1044, if mesh shroud material 1050 does not provide enough rigidity to bias first and second wire rings 1042, 1044 away from each other. For example, in FIG. 10B, four substantially equidistantly spaced stiffening members 1045 may extend from first wire ring 1042 to second wire ring 1044. Specifically, stiffening members 1045 may be seen to extend between the outer points of first and second wire rings 1042, 1044. Alternatively, in FIG. 10C, a coiled/spring like stiffening member 1047 may be seen to extend from first wire ring 1042 to second wire ring 1044. Stiffening member 1047 may be conically shaped to permit a close integration between an outside of stiffening member 1047 and an inside surface of wire mesh 1050. The above biasing characteristic is important when shroud 1040 is pulled proximally along guide wire 1018 toward and over fixed bristle element 1022 and sweep catheter 1030, as will be described below.

In FIG. 10A shroud portion 1040 may be advanced into position by one or more shroud control wires 1046, 1048, which may be feed through the hollow interior of sweep catheter 1030 parallel to guide wire 1018 and attached to opposite sides of second wire ring 1044, i.e., the distal ring. Although only two shroud control wires 1046, 1048 are shown, any number of generally equidistantly spaced wires may be used, so as to exert a substantially even pressure around second wire ring 1044. During operation of bristles 1032 to remove a blockage, shroud 1040 will be maintained at the position distal of the bristles until all of the brushing and cleaning operations are completed. Once this stage is reached, control wires 1046, 1048 may be used to retract shroud 1040 over fixed bristle element 1022 and bristles 1032 of sweep catheter 1030 by pulling a proximal end of each of control wires 1046, 1048 in the proximal direction.

As seen in FIGS. 10A-C, first and second wire rings 1042, 1044 of shroud 1040 are formed such that, at low temperature, e.g., at or about room temperature, the first and second wire rings 1042, 1044 may have a collapsed configuration approximating a cross or clover shape. Although not shown in FIG. 10A or 10B, cap 1020 may also be formed in a similar collapsed configuration. First wire ring 1048, i.e., the proximal ring, is generally slightly to somewhat larger in peripheral size then is second wire ring 38, i.e., the distal ring. The collapsed rings hold shroud 1040 in a substantially collapsed configuration as well.

Upon insertion through guide catheter 1016 into a bloodstream, shroud 1040 experiences an elevated temperature, as shown in FIG. 10A, and the memory metal making up first and second wire rings 1042, 1044, and cap 1020, if included, begins to expand, as shown in FIG. 10B, and ultimately transforms in shape to a substantially circular ring shape, as shown in FIG. 10C. This transformation effectively expands the volume contained within shroud 1040, and shroud 1040 takes on an approximately frustoconical shape. The length of shroud 1040 may preferably be approximately equal to the length of the axial extent of the bristles on fixed bristle element 1022 and on sweep catheter 1030.

Thermally-reactive shape memory metals are generally known in the art, an example of which is NITINOL (NIckel TItanium Naval Ordnance Laboratory), which is expected to be suitable for use in the present invention. Thermally-reactive shape memory metals operate to transform to an original shape, here a circular ring, linear stiffening member, spring/conically-coiled stiffening member, and a conical cap (if included), from a plastically deformed shape, e.g. the cross or clover shaped wire rings 1042, 1044, upon heating of the material.

In FIGS. 10A-C, mesh shroud material 1050 extending around and between first and second wire rings 1042, 1044 is sufficiently flexible so that it can elastically deform between the collapsed configuration (FIG. 10A) and the expanded configuration (FIG. 10C). The material may be a steel or polymer mesh, or any other flexible material that is compatible with the environment within the body of the patient. However, mesh shroud material 1050 may have disposed within it or on an exterior and/or interior surface the stiffening member, as described above. Alternatively, first and second wire mesh shroud material 1050 may also be made of a similar shape memory material as wire rings 1042, 1044, which, when expanded, provides sufficient longitudinal stiffness to permit shroud 1040 to be pulled over fixed bristle element 1022 and sweep catheter 1030 without collapsing and/or bunching.

Figure 11:
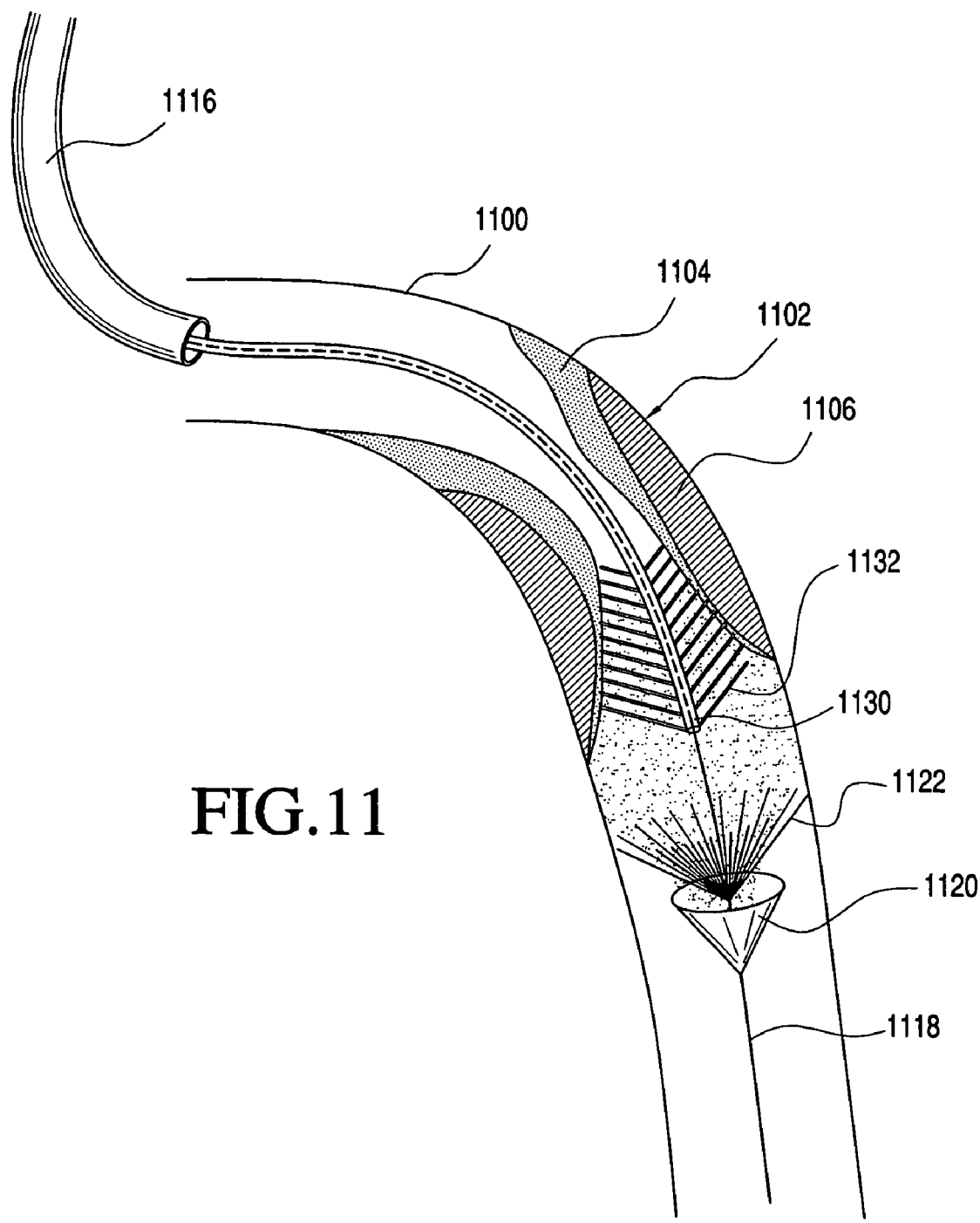
FIG. 11 is a simplified, partial cross-sectional side view of a catheter system disposed in a patient's artery to remove a thrombus attached to a wall of the patient's artery, in accordance with another embodiment of the present invention.

Most heart attacks involve a blockage or thrombus 102, as shown in FIG. 11, composed of a red, fibrin-rich, thrombus 1104, superimposed on a white, platelet-rich, thrombus 1106. In general, red thrombus 1104 is softer than white thrombus 1106. Bristles 1132 of a sweep catheter 1130 are sufficiently hard and stiff so as to be capable of scraping off or cutting off white thrombus 1106 as well as red thrombus 1104. As a result, this will provide the system and method of the present invention with an advantage over the use of clot dissolving medications, since such medications do not always work or do not work effectively on white thrombus 1106. Thus, the entire blockage will not generally be removed by using clot dissolving medications. The use of the different embodiments of the catheter system of the present invention also may avoids the risk engendered by the use of clot dissolving medications of potentially causing serious bleeding, possibly leading to lethal intracranial hemorrhaging.

The operation of the catheter system and the method for clearing a passage in a patient will now be discussed in greater detail in relation to FIGS. 1A-B and 10A-C. As noted earlier, the method may commence by the insertion of guide wire 18 to a position downstream of the blockage, e.g., thrombus 102, that is to be cleared. If the blockage is substantially a complete blockage, the guide wire itself may be used to pierce through the blockage, or another known technique may be used to initiate the clearing of the blockage.

Once guide wire 18 is in position, guide catheter 16 may be inserted along guide wire 18, with guide wire 18 thus extending through a channel in guide catheter 16. Guide catheter 16 generally has its distal end positioned upstream of the blockage at the origin of the artery that is to be cleared.

Sweep catheter 30 may be within the channel in guide catheter 16 and surrounding guide wire 18 when guide catheter 16 is inserted into the patient, or may be inserted through guide catheter 16 once guide catheter 16 is positioned proximal of thrombus 102. Similarly, fixed brush catheter 22 may be within guide catheter 16 either initially or after positioning of guide catheter 16. In general, the sweep catheter 30 has guide wire 18 and fixed brush catheter 22 extending through its hollow center, so as to permit sweep catheter 30 to rotate substantially freely within artery 100.

If the embodiment of the catheter system shown in FIG. 11, shroud 1040 and shroud control wires 1046, 1048 maybe inserted through guide catheter 1016 with the wires following along an inner wall of the guide catheter. As with the fixed brush catheter and sweep catheter, shroud 1040 may be within guide catheter 1016 when guide catheter 1016 is inserted, or may be advanced through guide catheter 1016 once the guide catheter has been positioned. Regardless of when shroud 1040 is advanced it, generally, is advanced through guide catheter 1016 before sweep catheter 1030 and shroud control wires 1046, 1048 are feed through the hollow interior of sweep catheter 1030 from the distal end to the proximal end.

In FIG. 10A, shroud 1040, fixed bristle element 1022, and sweep catheter 20 may be pre-positioned within guide catheter 1016, so that all of the elements are advanced with guide catheter 1016 to the desired position of guide catheter 1016. Upon attaining that position, shroud 1040 is advanced outwardly into the artery distal of the blockage fixed bristle element and sweep catheter 10. When these components are not pre-positioned within guide catheter 1016, it will be readily apparent that the sequence of insertion through the guide catheter should be selected so that shroud 1040 is first advanced into position, such that it is not interfered with by the bristles on the fixed brush catheter and the sweep catheter as it is moved into position.

In FIG. 1A, sweep catheter 30 is advanced such that the distal end of sweep catheter 30 with bristles 32 extends at least partially past the narrowest point in the opening through thrombus 102. The inclination of bristles 32 away from the tip of the distal end of sweep catheter 30 allows bristles 32 to fold back (not shown) toward the proximal end and to temporarily become parallel or almost parallel to the lengthwise direction of sweep catheter 30. In other words, as bristles 32 pass through the narrow part of the opening in thrombus 102, they readily bend to fit through the opening. However, when bristles 32 are pulled back in the proximal direction, the proximal inclination of bristles 32 tends to keep them from bending back in the distal direction to avoid the release of captured debris. Essentially, bristles 32 can more freely bend towards their acute angle side (i.e., proximally) than toward their obtuse angle side (i.e., distally). Additionally, the proximal inclination of bristles 32 allow them to accommodate the size of artery 100 such that one size or a small number of sizes may be sufficient (instead of requiring many different size heads for different size arteries). Also, the flexibility of bristles 32 and the portion of sweep catheter 30 to which they are fixed is such that damage to healthy tissue is avoided or minimized. To that end, the portion of sweep catheter 30 to which bristles 32 are fixed is preferably a traditional, known, flexible catheter material.

In embodiments with shroud 1040, in the initial stage of the blockage scraping or cutting operation, shroud 1040 and fixed brush catheter 1020 generally remain substantially stationary.

In FIG. 1, sweep catheter 30 is rotated and pulled back slowly toward the obstruction such that the smaller bristles 32 engage thrombus 102 first and sweep out the thrombus material enlarging the hole through it. As sweep catheter 30 continues to be pulled back or retracted, and rotating bristles 32 continue contacting the thrombus, the bristles of bristle 32 get progressively longer, so as to make the hole progressively larger, until all or essentially all of thrombus 102 is removed. Fixed bristle element 22 generally is constructed so as to trap freed material, such as platelets, in the bristles. For example, fixed bristle element 22 may have a number of individual bristles to provide a sufficient density and distribution for fixed bristle element 22. Alternatively, the trapping mechanism in fixed bristle element 22 may be similar to the engagement of fabric hooks and loops in hook-and-loop type fasteners such as those sold under the VELCRO trademark. Similarly, different materials with different degrees of hardness could be used for bristles 32 so as to most effectively remove thrombus 102 with no or minimal damage to arterial wall. The material used for bristles 32 may include the previously described various plastics and/or metals both with and without sputter coatings.

In FIG. 11, in addition to having fixed bristle member 32 trap the platelets and other removed material, guide catheter 16 may have an opening in its distal end to permit the suctioning of materials out of the patient through a suction channel 28 in FIG. 1, in catheter system 10.

As seen in FIG. 11, suction channel 28 may be provided as an integral part of guide catheter 16. Suction channel 28 may further encircle a central guide channel 36, through which guide wire 18, shroud 1040 fixed brush catheter 22, and sweep catheter 30 may extend. Guide channel 36 is preferably supported in position by plurality of radially extending ribs 31 which space guide channel 36 from the wall of guide catheter 30. This annular space operates as suction channel 28.

As the thrombus material is separated from wall 104 of the blood vessel 100 in the vessel clearing process, in FIG. 1 suction pump 40 may be used to draw the material through suction channel 28 in the guide catheter, so that the majority of the removed material will not flow downstream of thrombus 102. The material that is not removed by suctioning will generally travel downstream, and will be intercepted by the bristles of fixed brush catheter 22, and thus the amount of material permitted to flow further downstream in the blood vessel will be maintained to a minimum. In addition, this will restrict particles to an acceptable size that can be accommodated by the distal circulation system to prevent causing a subsequent blockage.

Once the brushing operation is completed, in FIG. 1A, sweep catheter 30 and fixed brush catheter 22 are to be retracted into guide catheter 16 for removal from the blood vessel of the patient. The retraction of these items, each of which has at least some bristles which extend out to the walls of the artery, has a tendency to agitate the bristles as they catch and release on the walls of the blood vessel. This can cause the bristles to release some or all of the removed material that had been trapped by the bristles; and the material can then travel through the bloodstream.

In order to substantially prevent this undesirable effect, prior to sweep catheter 30 and fixed brush catheter 22 being retracted, in FIG. 1A, cap 20 is pulled toward the distal end of guide catheter 16. As cap 20 is pulled toward the distal end of guide catheter 16, cap 20 contacts the bristles of fixed brush catheter 22 and sweep catheter 30, to "fold" the flexible bristles proximally toward a substantially parallel orientation with respect to the catheter or wire on which they are mounted. Similarly, in the system in FIGS. 10A-C, when shroud 1040 is pulled toward the distal end of guide catheter 16, shroud 1040 envelops the bristles of fixed brush catheter 22 and sweep catheter 30 to "fold" the flexible bristles into a substantially parallel orientation with respect to the catheter or wire on which they are mounted. The bristles thus retain any material trapped thereby, and shroud 1040 provides a further barrier for trapping the material, should the material be released from any of the bristles. Shroud 1040 additionally decreases the effective cross-section of the sets of bristles, such that there is a reduced possibility of encountering a vessel wall upon retraction into guide catheter 1016.

Although specific constructions have been presented herein, it is to be understood that these are for illustrative purposes only. Various modifications and adaptations will be apparent to those of skill in the art. In view of possible modifications, it will be appreciated that the scope of the present invention should be determined by reference to the claims appended hereto.

What is claimed is:

1. A system for widening passages in the body of a patient comprising:

a member extendable into a pre-existing passage of the patient, said member having a proximal end and a distal end with a hollow interior extending therebetween;

moveable bristles disposed on the member adjacent the distal end such that rotation of the proximal end of the member causes rotation which, in turn, rotates the bristles, the bristles being operable upon rotation to remove material from walls of the pre-existing passage within which the bristles rotate and, said bristles being inclined away from the distal end of the member;

a guide wire having a proximal end and a distal end being movably disposed within the hollow interior of the member and extendable into the patient and at least one channel running longitudinally along a portion of the guide wire;

a non-rotating capture member coaxially aligned with, fixed to and near the distal end of the guide wire and adapted to be disposed within the hollow interior of the member and extendable into the patient beyond the distal end of the member by the guide wire, the capture member comprising non-rotating bristles that are circumferentially aligned around and fixed to an annular ring positioned around and coaxially aligned with the guide wire and having at least one tab on an inner edge of the annular ring where the at least one tab slidingly engages the at least one channel in the guide wire and the non-rotating bristles are to capture the material removed from the walls of the pre-existing passage in the patient; and a cap with an open-ended conical shape that is open toward the proximal end of the guide wire and that is coaxially aligned with and attached to the guide wire distal of the non-rotating bristles and the at least one channel.

2. The system of claim 1 wherein the system is a catheter system and the member is a sweep catheter with the bristles attached to the distal end thereof; and the catheter system is operable to remove obstructions from the patient's vascular system and the bristles are operable to remove material from walls of the pre-existing passage in the patient's vascular system.

3. The catheter system of claim 2 wherein the bristles extend out at an angle from the member such that material removed from the walls of the pre-existing passage in the patient's vascular system is pushed back in a proximal direction away from the distal end of the sweep catheter by operation of the distal end of the sweep catheter.

4. The catheter system of claim 3 further comprising a suction applicator operable to apply a suction adjacent the distal end of the sweep catheter.

5. The catheter system of claim 3 further comprising a guide catheter, a portion of the sweep catheter being inside the guide catheter, the sweep catheter extending out of a distal end of the guide catheter; the suction applicator including a pump at a proximal end of the guide catheter and a suction channel operably connected to the pump in the guide catheter; and suction is applied adjacent the distal end of the sweep catheter by operation of the pump acting through the suction channel.

6. The catheter system of claim 5 further comprising a rotator operable to rotate the proximal end of the sweep catheter, a portion of the sweep catheter being inside the guide catheter, the sweep catheter extending out of a distal end of the guide catheter.

7. The system of claim 1 wherein the non-rotating bristles extend out from the guide wire at an angle toward the proximal end of the guide wire.

8. The system of claim 7 wherein the non-rotating bristles extend out and contact around an entire circumference of an interior wall of the pre-existing passage in the patient to form a porous barrier to catch the material removed from the walls of the passage.

9. The system of claim 8 wherein a density of the non-rotating bristles determines the size of material particles to be screened.

10. The system of claim 1 wherein the cap comprises a solid, non-biologically reactive material.

11. The system of claim 10 wherein the non-biologically reactive material comprises at least one of a metal, an alloy, and a plastic.

12. The system of claim 10 wherein the cap comprises a deformable, shape memory material.

13. The system of claim 1 wherein the cap comprises a rigid-mesh, non-biologically reactive material.

14. The system of claim 13 wherein the non-biologically reactive material comprises at least one of a metal, an alloy, and a plastic.

15. The system of claim 13 wherein the cap comprises a deformable, shape memory material.

16. The system of claim 1 wherein the cap is moveable distally and proximally with respect to the non-rotating bristles.

17. The system of claim 16 wherein the cap comprises a solid, deformable, thermal-shape memory material open-ended cone.

18. The system of claim 16 wherein the cap is biased away from the non-rotating bristles.

19. The system of claim 16 wherein the cap is moveable in the proximal direction to surround a distal end of the non-rotating bristles and to cause the non-rotating bristles to angle farther backward toward the proximal end of the guide wire to hold any removed material trapped therein.

20. The system of claim 19 wherein causing the non-rotating bristles to angle farther backward causes the density of the bristles to become greater and prevent the trapped material from escaping.

21. The system of claim 1 wherein the cap comprises a porous cap with an open proximal end and a substantially closed distal end coaxially aligned with and attached to the guide wire.

22. The system of claim 21 wherein the porous cap has a substantially conical shape.

23. The system of claim 22 wherein the porous cap is adapted to fit within the hollow interior of the member and to open after being pushed out of the member by the guide wire and to expand to contact an interior surface of the pre-existing passage in the patient in which the system has been inserted.

24. The system of claim 23 wherein the porous cap acts to trap the removed material that contacts the porous cap.

25. The system of claim 21 wherein when the porous cap with an open proximal end is moved proximally and contacts the bristles adjacent the distal end of the member, the bristles fold back toward the guide wire.

26. The system of claim 21 wherein the porous cap comprises a deformable, shape-memory mesh of a non-biologically reactive material.

27. The system of claim 26 wherein the non-biologically reactive material comprises at least one of a metal, an alloy, and a plastic.

28. The system of claim 1 wherein the bristles include a sputter-coating of at least one of carbon, gold and diamond.

29. A method of removing material from walls of passages in a patient's vascular system, the method comprising:

extending a member into a passage in the patient's vascular system in a position distal to a material buildup in the passage, the member having a proximal end, a distal end with a tip, a hollow interior extending between defining openings at the proximal and distal ends, the member having bristles attached to an exterior surface at its distal end;

providing a guide wire having a proximal end and a distal end within the hollow interior of the member, said guide wire comprising at least one channel running longitudinally along a portion of the guide wire;

extending a capture member into the patient's vascular system from within the hollow interior of the member and distal of the bristles on the distal end of the member so that a first part of the capture member expands out and closes off the passage to trap particles removed from the material buildup, the capture member comprising non-rotating bristles that are circumferentially aligned around and fixed to an annular ring positioned around and coaxially aligned with the guide wire and having at least one tab on an inner edge of the annular ring where the at least one tab slidingly engages the at least one channel in the guide wire and the non-rotating bristles are to capture the material removed from the walls of the pre-existing passage in the patient;

extending a cap with an open-ended conical shape from within the hollow interior of the member, said cap being open toward the proximal end of the guide wire and coaxially aligned with and attached to the guide wire distal of the non-rotating bristles and the at least one channel rotating the proximal end of the member to cause rotation of the distal end of the member and in turn rotate the bristles such that the bristles remove particles of material from a wall of the passage in the patient and force substantially all of the removed particles in the proximal direction;

optionally suctioning the removed particles of the material buildup from the passage adjacent the distal end of the member;

filtering some or substantially all of the removed particles of the material buildup in the passage with the capture member; and closing the capture member to hold the filtered particles of material buildup in the capture member by retracting the conical cap proximally such that a distal end of the at least one channel moves toward the at least one tab.

30. The method of claim 29 further comprising:
removing the member and the capture member from the passage in the patient's vascular system.

31. The method of claim 30 wherein the bristles used on the member are inclined away from the tip of the distal end of the member and toward the proximal end of the member as they extend out from the distal end of the member.

32. The method of claim 31 wherein retracting the capture member proximally comprises:
moving a guide wire attached to a second part of the capture member in a proximal direction to close the first part of the capture member and to close the bristles on the member.

33. The method of claim 32 wherein removing the member and the capture member comprises:
moving the guide wire, a separate central wire attached to the first part of the capture member and a sweep catheter attached to the member in a proximal direction.

34. The method of claim 33 wherein the guide wire moves within a hollow interior of the separate central wire.

35. The method of claim 29 wherein closing the capture member comprises:
moving a second part of the capture member in a proximal direction to contact and close the first part of the capture member.

36. The method of claim 29 wherein the non-rotating bristles extend out from the guide wire at an angle toward the proximal end of the guide wire.

37. The method of claim 36 wherein the non-rotating bristles extend out and contact around an entire circumference of an interior wall of the pre-existing passage in the patient to form a porous barrier to catch the material removed from the walls of the passage.

38. The method of claim 37 wherein a density of the non-rotating bristles determines the size of material particles to be screened.

* * * * *